(12) United States Patent
Morrison (10) Patent No.: US 7,357,896 B2
(45) Date of Patent: Apr. 15, 2008

(54) RESISTOMETER

(75) Inventor: Todd Morrison, Dana Point, CA (US)

(73) Assignee: Ethicon, Inc., Somerville, NJ (US)

( * ) Notice: Subject to any disclaimer, the term of this patent is extended or adjusted under 35 U.S.C. 154(b) by 654 days.

(21) Appl. No.: 10/609,771

(22) Filed: Jun. 30, 2003

(65) Prior Publication Data

US 2004/0265945 A1    Dec. 30, 2004

(51) Int. Cl.
*A61L 2/24* (2006.01)
*A61L 2/20* (2006.01)
*A61L 2/14* (2006.01)
*B32B 5/18* (2006.01)
*G01N 33/18* (2006.01)

(52) U.S. Cl. .............. 422/3; 422/79; 435/31; 435/287.4; 436/62

(58) Field of Classification Search ............ 422/3, 422/22, 28, 119, 292, 79; 73/863.01, 864.83, 73/426; 435/31, 287.4; 436/62
See application file for complete search history.

(56) References Cited

U.S. PATENT DOCUMENTS

| | | | |
|---|---|---|---|
| 4,801,421 A | 1/1989 | Ackerson et al. | |
| 4,973,449 A | 11/1990 | Kolstad et al. | |
| 5,482,684 A | 1/1996 | Martens et al. | |
| 5,656,238 A | 8/1997 | Spencer et al. | |
| 5,667,753 A | 9/1997 | Jacobs et al. | |
| 6,156,267 A * | 12/2000 | Pai et al. | 422/3 |
| 6,269,680 B1 | 8/2001 | Prieve et al. | |
| 6,447,719 B1 | 9/2002 | Agamohamadi et al. | |
| 6,537,491 B1 * | 3/2003 | Wang et al. | 422/3 |
| 6,852,277 B2 * | 2/2005 | Platt et al. | 422/3 |
| 2002/0160440 A1 | 10/2002 | McDonnell et al. | |
| 2003/0086820 A1 | 5/2003 | McDonnell et al. | |

OTHER PUBLICATIONS

International Search Report EP 04 25 3886 dated Oct. 8, 2004.
S. Schaffer et al., "Vaporized Hydrogen Peroxide at Low Pressures as an Agent to Kill Bacterial Spores", Zentral Sterilisation, no date.
"BIER/EO gas vessels", Association for the Advancement of Medical Instrumentation, ANSI/AAMI ST44-1992, pp. 653-670.
"BIER/Steam vessels", Association for the Advancement of Medical Instrumentation, ANSI/AAMI ST45-1992, pp. 671-683.

* cited by examiner

*Primary Examiner*—Gladys J P Corcoran
*Assistant Examiner*—Kevin Joyner (57) ABSTRACT

A Biological Indicator Evaluator Resistometer (BIER vessel) provides enhancements in controlling the start and end points of exposure to a sterilant gas. The end point control employs a large volume relative to the test chamber volume upon which is drawn a deep vacuum and then exposed to the test chamber to quickly exhaust the sterilant gas from the test chamber.

22 Claims, 7 Drawing Sheets

RESISTOMETER

BACKGROUND OF THE INVENTION

The present invention relates to a Biological Indicator Evaluator Resistometer (BIER) vessel system and related resistometers primarily for testing indicators, such as biological or chemical indicators, and process challenge devices in sterilization and disinfection systems.

Biological indictors are used to confirm the efficacy of a sterilization procedure, such as a vapor phase chemical sterilization system. One popular vapor phase chemical sterilization system employs vapor phase hydrogen peroxide, preferably with a plasma at some point during the exposure to hydrogen peroxide to enhance the cycle efficiency and eliminate hydrogen peroxide residuals. Other vapor phase systems include peracetic acid, ozone, chlorine dioxides ethylene dioxide and others. Instruments to be sterilized in such a cycle are typically placed into a chamber and exposed to the vapor phase sterilizing agent. To insure that the procedure worked as intended one or more biological indicators are typically included with the load.

A biological indicator typically comprises a quantity of a viable test microorganisms which if killed during the sterilization procedure indicate that it worked properly. Other indicators may also be included such as chemical exposure indicators which provide an indication of the exposure, or the level of exposure, of the load to the sterilizing agent. These indicator devices themselves must be tested to insure that they provide a standardized response which is accurate and reproducible. Such testing may include testing variations in the design or manufacturing of the indicator and production sample testing.

Further, it is often desirable to experiment with variations in sterilization cycle parameters and to examine the effects of these variations with a high degree of accuracy.

To achieve these goals, a BIER vessel is sometimes used. A BIER vessel has a first chamber in which a sterilizing atmosphere can be created and a second chamber that is isolated from the first chamber while the sterilization atmosphere is created. The first and second chambers can be quickly placed into fluid communication with each other to quickly create a known sterilization environment in the second chamber without going through a protracted process of gradually adjusting the conditions therein. For instance, rather than gradually admitting, vaporizing and diffusing a vapor phase sterilent such has hydrogen peroxide throughout a chamber, by removing a partition between the first and second chambers the vapor phase hydrogen peroxide in a first chamber will quickly establish itself within the second chamber thus creating a reliable starting time for evaluating the sterilization procedure and its effects upon a biological or chemical indicator being tested.

SUMMARY OF THE INVENTION

A sterilization or disinfection test system according to the present invention comprises a first compartment having a first volume and a second compartment having a second volume. A vacuum source connects to the second chamber not through the first chamber. The vacuum source comprises a third volume which is at least five times as large as the second volume. A first openable separation between the first compartment and the second compartment and a second openable separation between the vacuum source and the second volume.

The test system has several uses including testing indicators such as biological or chemical exposure indicators or challenge packs (a pack having a diffusion restriction of some form leading to the indicator). The test system can also be helpful in evaluating sterilization cycles and in designing new sterilization cycles.

Preferably, the third volume is at least ten times as large as the second volume, and more preferably at least twenty times as large as the second volume.

A plasma generator can be associated with one or both of the first and second chambers, preferably the first chamber.

Preferably, the first volume is at least ten times as large as the second volume.

Preferably, a vent valve is associated with the second compartment, and a control system associated with the vent valve wherein the vent valve can vent the system to a pressure lower than atmospheric pressure under the control of the control system.

Preferably, a monitor is associated with the second compartment capable of monitoring sterilant levels within the second compartment. It is also desirable to have a temperature sensor and a pressure sensor associated with the second compartment, and moreover a humidity sensor.

Preferably, a one or more additional compartments connect to the first compartment, each being separated therefrom by its own openable separation, and more preferably each having its own vent valve and including a control system capable of independently controlling each of the vent valves associated with the additional compartments.

A method for providing a controlled sterilization or disinfection process suitable for collecting testing data comprises the steps of:

providing a sterilizing environment comprising a vapor sterilant into a first chamber;

placing a test device in a second chamber;

opening a partition between the first chamber and the second chamber and thereby subjecting the second chamber to the sterilizing environment;

isolating the second chamber from the first chamber; and after a predetermined time, quickly terminating exposure of the chemical sterilant to the test device, wherein the step of quickly terminating the exposure of the chemical sterilant to the test device comprises withdrawing the chemical sterilant from the second chamber by exposing the second chamber to a source of vacuum which comprises a third volume at least five times as large as the second volume.

Preferably, the third volume is at least ten times as large as the second volume, and more preferably at least twenty times as large as the second volume.

The step of quickly terminating the exposure of the chemical sterilant to the test microorganism can comprise applying a plasma to the second chamber, preferably generated in the first chamber and then admitted into the second chamber.

At some time prior to the predetermined time, the second space can be vented to a pressure lower than atmospheric pressure.

Preferably, sterilant levels are monitored within the second compartment.

The test device can comprise a biological indicator, a chemical indicator, a process challenge device, or instrumentation to record test data.

A further sterilization or disinfection test system according to the present invention comprises a first compartment having a first volume, a second compartment having a second volume, and an openable separation between the first compartment and the second compartment. A first sterilant monitor is associated with the first compartment and a second sterilant monitor is associated with the second compartment.

A further method for providing a controlled sterilization or disinfection process suitable for collecting testing data comprises the steps of:

providing a sterilizing environment comprising a vapor sterilant into a first chamber;

opening a first partition between the first chamber and the second chamber and thereby subjecting the second chamber to the sterilizing environment; and independently monitoring a concentration of sterilant in the first and second.

DETAILED DESCRIPTION

Figure 1:
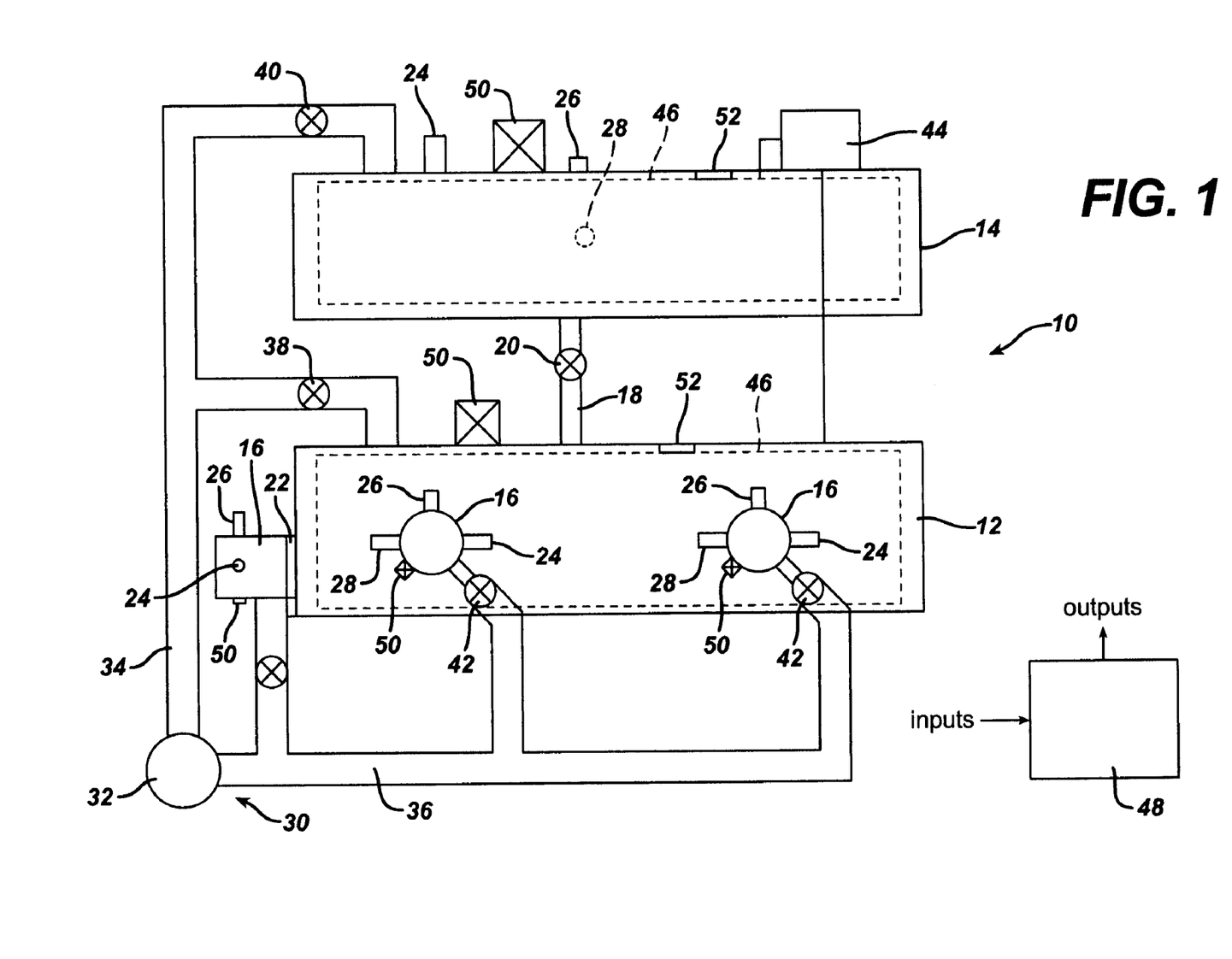
FIG. 1 is a block diagram of a BIER vessel according to the present invention.

FIG. 1. discloses in block diagram format an improved BIER vessel 10 according to the present invention. The BIER vessel 10 comprises a first chamber 12 typically employed as a vaporization chamber and a second chamber 14 typically employed as a test chamber. In this example the chambers 12 and 14 are of similar size, however their sizes can be varied to accommodate individual needs. A plurality of test chambers 16 attach to the vaporization chamber 12. These test chambers 16 are much smaller in size then the vaporization chamber 12 whereby upon placing the test chamber 16 into communication with the vaporization chamber 12 the conditions of the vaporization chamber 12 are quickly established within the test chamber 16 to provide an accurate starting point for a test. The most desirable starting point in a test would have the concentration of vaporized sterilant in the test chamber 16 change instantaneously from zero to the desired test concentration. A conduit 18 connects the first chamber 12 and second chamber 14 and incorporates an isolation valve 20 to separate the first chamber 12 from the second chamber 14. Similarly, each of the test chambers 16 are isolated from the first chamber 12 by an isolation valve 22.

Monitoring of conditions within the BIER vessel system 10 helps assure that the process is proceeding as desired. A separate pressure monitor 24, temperature sensor 26 and sterilant concentration monitor 28 is provided for each of the first chamber 12, second chamber 14 and test chambers 16. Sterilant monitors for hydrogen peroxide preferably employ light absorption techniques, such as described in the Prieve et al. U.S. Pat. No. 6,269,680, incorporated herein by reference.

A vacuum system 30 comprises vacuum pump 32 and vacuum lines 34 from the vacuum pump 32 to the first and second chambers 12 and 14 and vacuum lines 36 serving the smaller test chambers 16. Vacuum vent valves 38 and 40 on the first chamber and second chamber 12 and 14, respectively isolate these chambers from the vacuum line 34 and vacuum vent valves 42 isolate the smaller test chambers 16 from the vacuum lines 36. The volume of the vacuum lines 36 exceeds the volume of their associated test chamber 16 such that upon opening the vent valves 42 contents of the test chamber 16 are quickly evacuated. When this occurs at the end of an exposure period to a sterilant, the concentration of sterilant in the test chamber 16 is quickly diminished so as to provide a controllable end point the exposure period. Similar to the starting point, the most desirable end point would have the sterilant concentration drop from the desired testing concentration to zero instantaneously.

A plasma generator 44 connects to electrodes 46 in the first and second chambers 12 and 14 provide the capability of driving the gases therein into the plasma state. The electrodes 46 are isolated from their respective chambers 12 and 14 and the plasma generator 44 applies an electrical potential between the electrode 46 and the respective test chamber 12 or 14. Examples of appropriate plasma generation systems are described in U.S. Pat. Nos. 4,801,421, 5,656,238 and 6,447,719, incorporated herein by reference.

A control system 48 interconnects to the various sensors 24, 26, 28, valves 20, 22, 38, 40, 42, the plasma generator 44 and the vacuum system 30 and other equipment as may be needed or desired to affect control over the process of the BIER vessel 10. Preferably, the control system includes data storage and networking capabilities for easy handling of the test data.

Vent valves 50 are provided on each of the chambers, 12, 14 and 16 to allow venting of the chamber to atmospheric pressure or a target pressure below atmospheric. These vent valves 50 are also connected to, and are under the control of the control system 48. Preferably they comprise a dual valve couple, one being larger than the other, to provide quick venting of large volumes and fine tuning of desired pressure. They are cycled open and closed until the target pressure is reached. A separate injector 52 is provided for first chamber 12 and second chamber 14, through which a pre-measured quantity of liquid sterilant solution can be injected via a syringe through a septum and then vaporized into the chamber 12 or 14.

Figure 2:
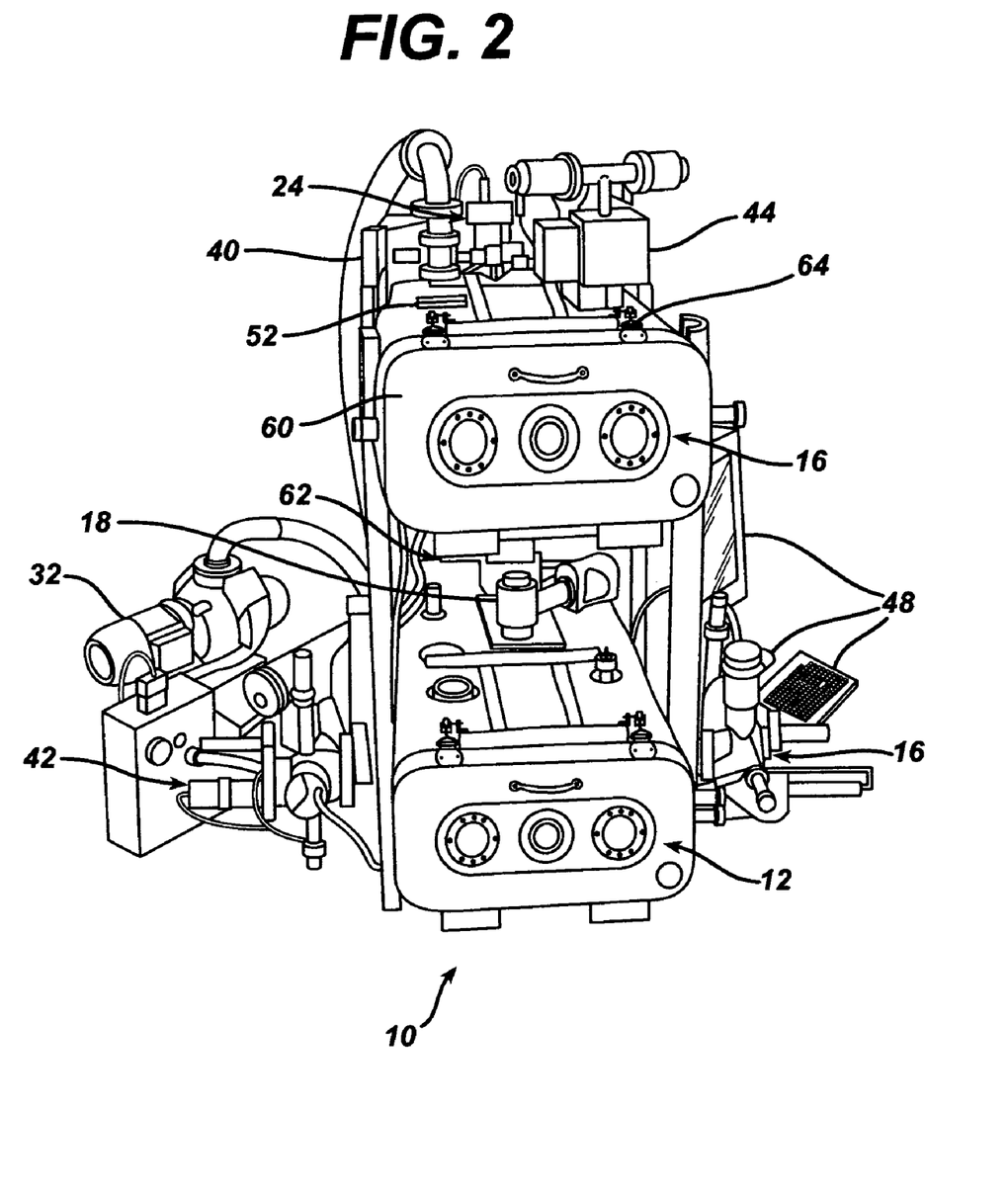
FIG. 2 is a perspective view of the BIER vessel of FIG. 1.
Figure 3:
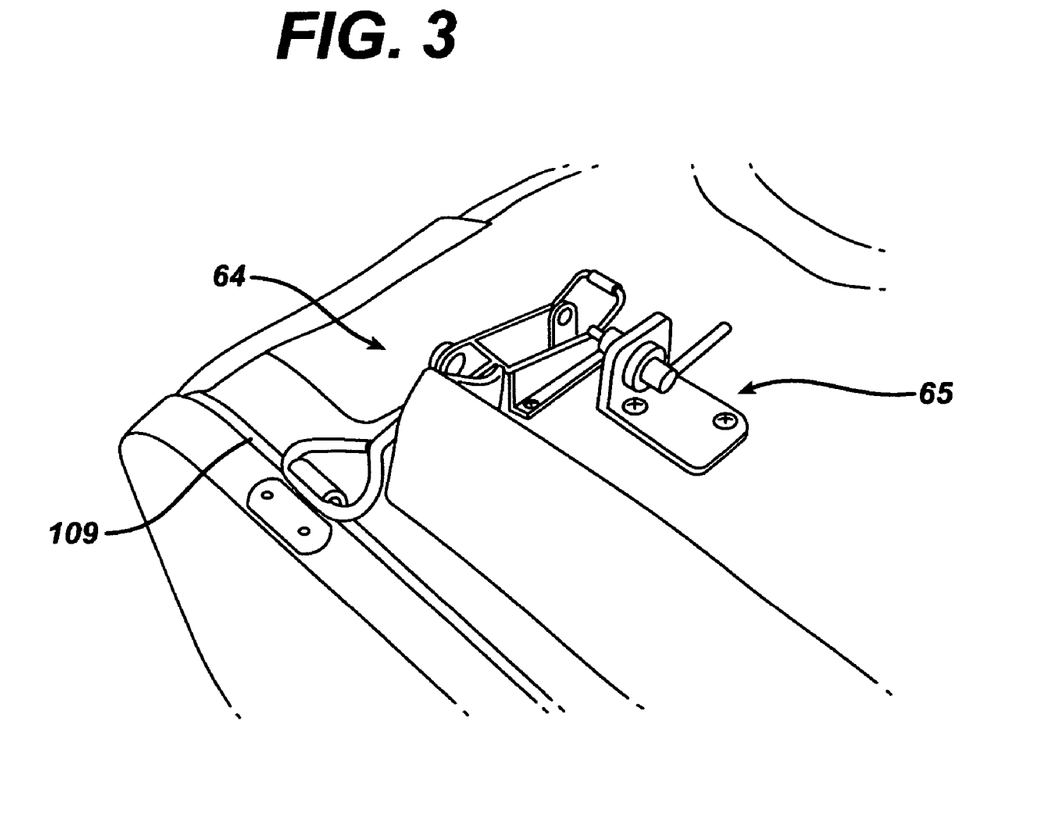
FIG. 3 is a detailed perspective view of a latch mechanism on the BIER vessel of FIG. 1.

FIG. 2 shows in perspective view the BIER vessel 10 depicted in block diagram form in FIG. 1. Each of chambers 12 and 14 has a large door 60 having a floating hinge mechanism 62 and interlocking latch 64. The latch 64 is connected to the control system 48 and plasma generator 44 to extinguish the plasma if the door 60 is opened during the cycle when there is plasma present or when the concentration of sterilant is too high. As also seen in FIG. 3, a pneumatic piston 65, under control of the control system 48, extends over the latch 64 to prevent opening of the latch during unsafe conditions.

Figure 4:
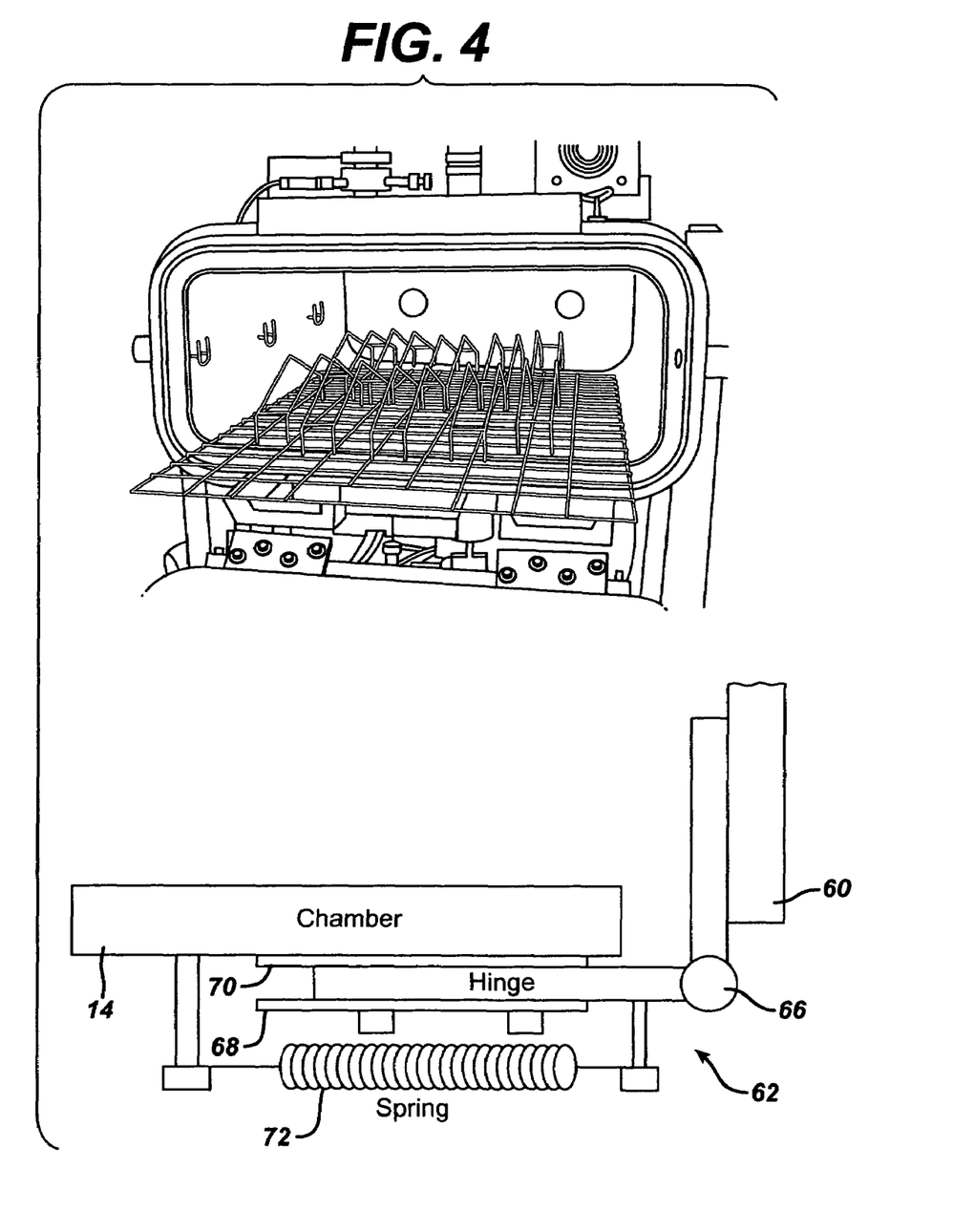
FIG. 4 is cross-sectional view taken along lines 4-4 of FIG. 2 showing a spring-loaded floating hinge.

FIG. 4 shows the hinge mechanism 62 which comprises a hinge 66 attached to the door 60 and slideably attached to the outer wall of the chamber 12 or 14. The hinge 66 is trapped between an outer plate 68 and an inner plate 70' while retaining freedom to slide therebetween. Preferably, the plates 68 and 70 are formed out of or coated with a low friction substance such as polytetrafluoroethylene (PTFE). A spring 72 biases the hinge toward the chamber 12 or 14. When the door 60 is closed, the spring normalizes the forces applied at the top and bottom of the chamber 12 or 14.

Figure 5:
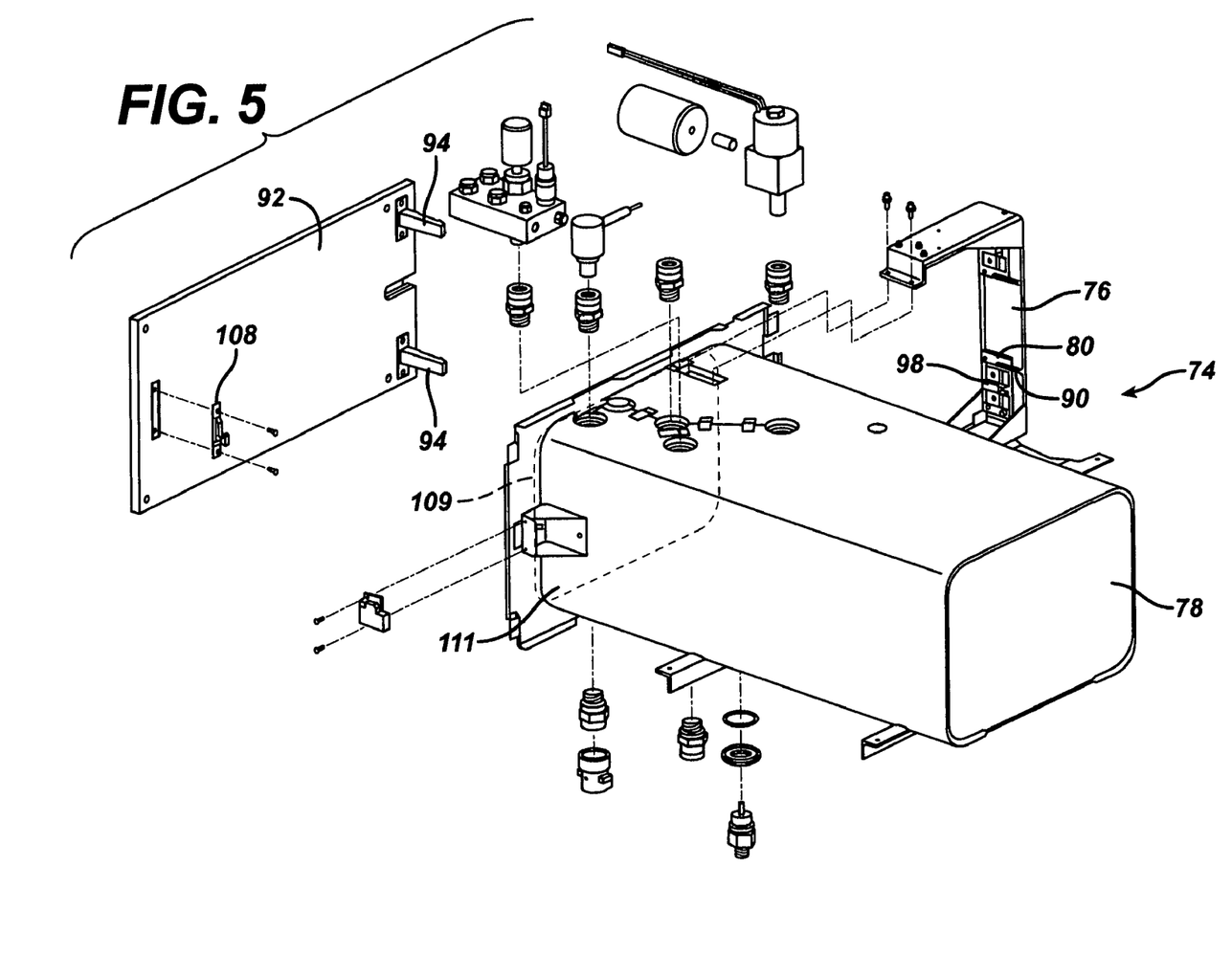
FIG. 5 is an exploded perspective view of an alternative spring-loaded floating hinge mechanism.
Figure 6:
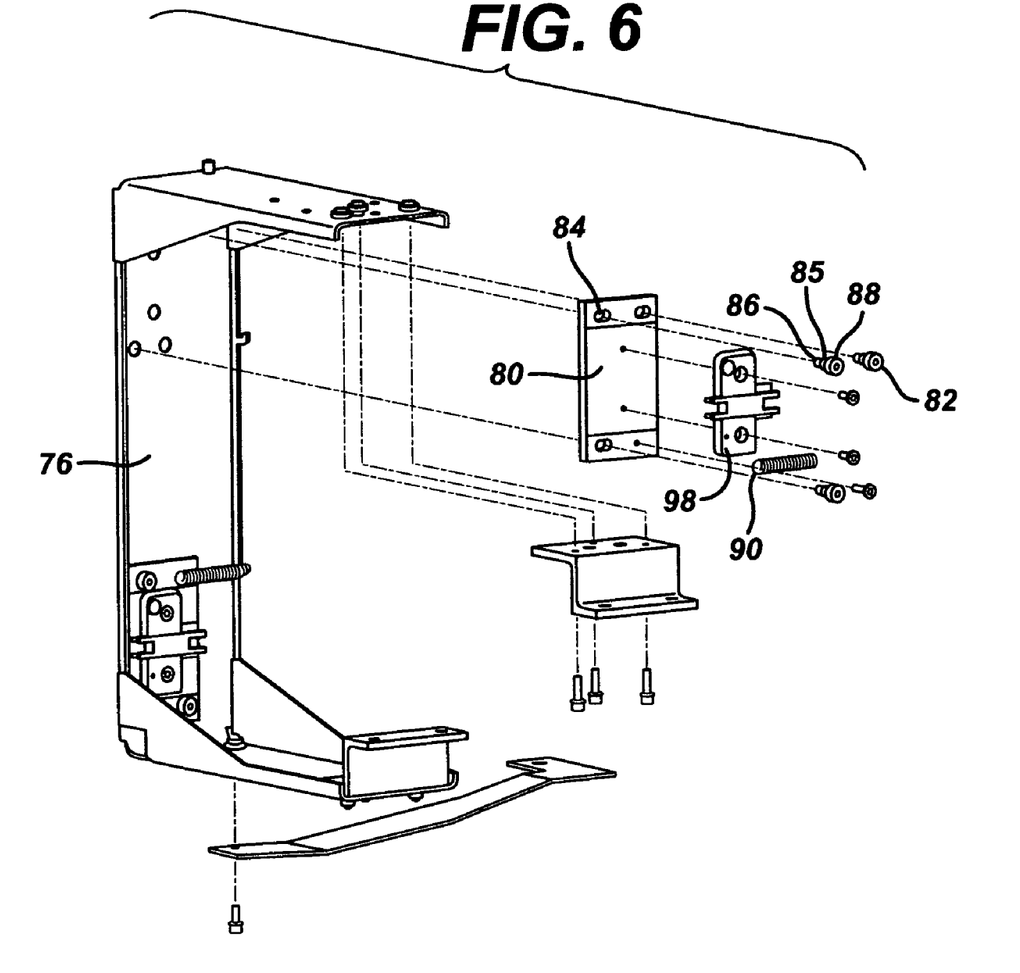
FIG. 6 is an exploded perspective view of a mounting bracket of the hinge mechanism of FIG. 5.
Figure 7:
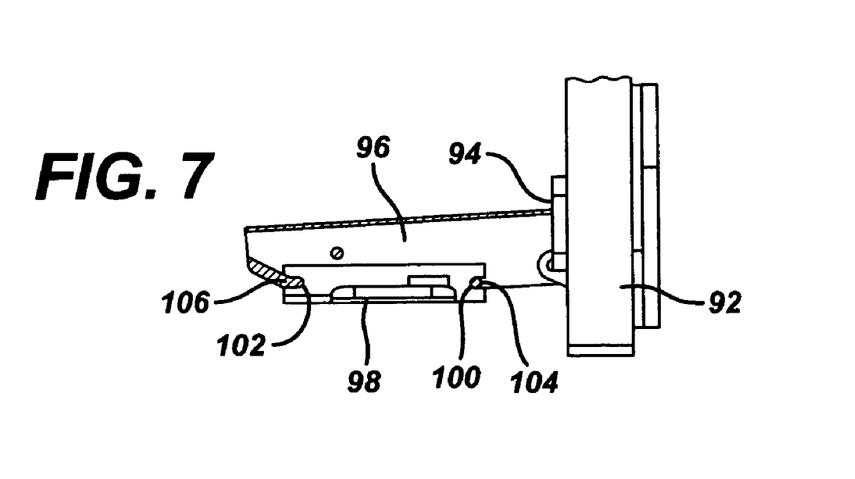
FIG. 7 is a side elevation view of a hinge attachment mechanism of the hinge mechanism of FIG. 5.

FIGS. 5 to 7 show an alternative version hinge mechanism 74. A hinge mounting bracket 76 affixes to a chamber 78. Two mounting plates 80 connect to the bracket 76 via screws 82 passing through elongated slots 84 in the mounting plate 80 so as to provide a limited degree of lateral movement of the plate 80 relative to the bracket 76. The screws 82 comprise an unthreaded shoulder 85 between machine threads 86 and a head 88 to allow easy movement of the shoulder 85 within the slots 84. A spring 90 biases the mounting plate 80 away from a door 92.

Two hinges 94 attach to the door 92 and have connectors 96 extending therefrom toward the mounting plates 80. A clip plate 98 attaches to each mounting plate 80 and has rear notches 100 and front notches 102 into which snap respectively a proximal pin 104 and distal catch 106 on the connectors 96 thus allowing easy attachment and detachment of the door 92. A latch 108 is provided on a side of the door 92 opposite the hinges 94. A seal 109 about an, opening 111 into the chamber 78 and between the door 92 and the chamber 78 helps preserve a vacuum in the chamber 78.

Although the hinges 94 are shown slidably attached to the chamber 78, one of skill in the art would see that their design could be modified to slidably attach the hinges 94 to the door 92. Further, rather than allow movement at the hinges to normalize forces on the door seal 109, movement could instead be provided at the latch 108 or at both the latch 108 and the hinges 94.

Figure 8:
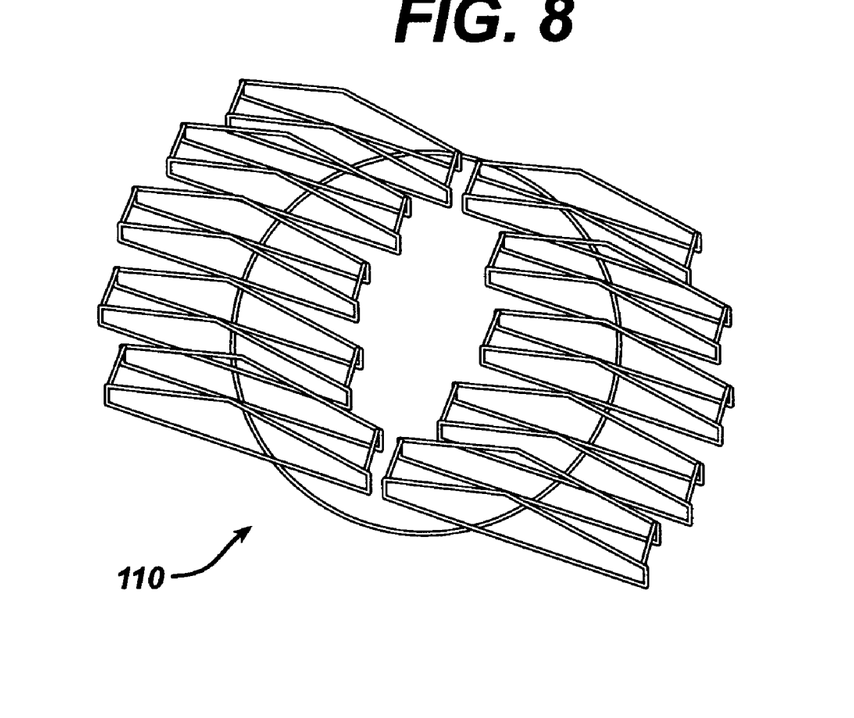
FIG. 8 is a perspective view of a sample rack for use within the BIER vessel of FIG. 1.
Figure 9:
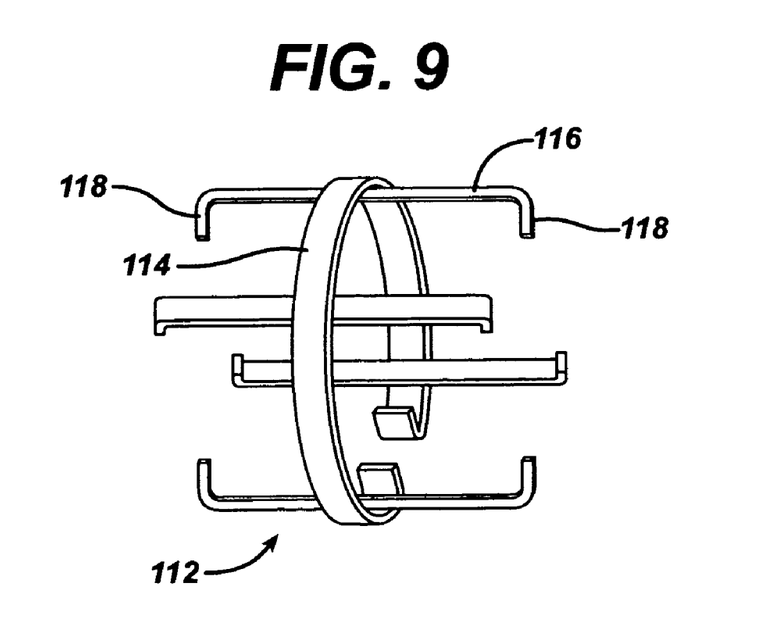
FIG. 9 is a perspective view of an alternative sample rack for use within the BIER vessel of FIG. 1

Test racks for holding biological indicators are helpful in getting even distribution of the indicators within the test chambers 14 and 16. FIG. 8 shows a rack 110 suitable for holding twenty flat test packs (not shown), each containing a biological indicator, for use within the large test chamber 14. FIG. 9 shows a rack 112 suitable for holding four biological indicators within the cylindrical test chamber 16. An open circular ring 114 having evenly spaced holder 116 about its circumference fits snugly within the test chamber 16. Each holder 116 has a pair of end flanges 118 between which can be placed a biological indicator.

A typical cycle in the BIER vessel 10 comprises the following.

Heat all portions of the BIER Vessel 10 to 50° C. OPTIONALLY: Heat the vaporizer chamber 12 to 65° C., the large test chamber 14 to 50° C., and the small test chambers or ports 16 to 45° C. The temperature differentials cause small pressure gradients in the gas which can be manipulated to help control gas flow.

Evacuate all portions of the BIER Vessel to 0.2 Torr and light a plasma. The vacuum and plasma both aid in eliminating any possible residuals, such as water or sterilant from a prior cycle, in the vessel. As plasma energy creates heat, the pressure may rise. The 0.2 Torr pressure can be maintained with the throttling valves 50 that opens and closes to raise or lower pressure.

Vent all chambers 12, 14 and 16 to atmospheric pressure and load samples. Samples are preferably positioned within all portions of the chamber 14 so that when sterilant is introduced into the portions, it exposes all samples equally.

Evacuate all portions of the BIER Vessel 10 to 0.2 Torr. The vacuum enhances sterilant vaporization and diffusion. OPTIONALLY: Plasma may be introduced to condition/heat the samples/load. Stop the plasma at the end of the conditioning time.

Close respective valves to isolate all portions of the BIER vessel 10 at the 0.2 Torr pressure.

Introduce sterilant, such as 59% hydrogen peroxide solution, into the vaporizer chamber 12 until the desired concentration is reached, as detected by the sterilant monitor 28 therein. If too much is accidentally introduced, a small portion can be evacuated out. The addition and removal of sterilant can be manipulated until the desired sterilant concentration and pressure is achieved.

The sterilant in the vaporizer chamber 12 will cause the pressure to rise higher than the other portions of the vessel that are currently at 0.2 Torr. Once the valves 20 or 22 isolating the other portions of the vessel are opened, the pressure (and temperature) differentials will immediately force the sterilant into the other portions of the vessel. OPTIONALLY: The valves 22 do not have to be opened or closed simultaneously, allowing for different exposure times for different samples.

At the end of the desired exposure time, evacuate the vessel portions to 0.2 Torr to remove the remaining sterilant before opening the doors to remove the samples. The evacuation time will be less than 30 seconds for the chambers and less than 5 seconds for the Ports. Optionally, plasma may be introduced to enhance the removal of sterilant residual.

Quickly vent the portions of the vessel to allow the filtered air rushing in to "scrub" the surfaces, freeing sterilant that was being held by other materials, and remove the samples/load. Test the biological indicators.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. A sterilization or disinfection test system, the system comprising:
    a first chamber having a first volume and a second chamber having a second volume;
    a vacuum source connected to the second chamber not through the first chamber;
    the vacuum source comprising a third volume, the third volume being at least five times as large as the second volume; and
    a first openable barrier between the first chamber and the second chamber and a second openable barrier between the vacuum source and the second chamber.

2. A system according to claim 1 wherein the third volume is at least ten times as large as the second volume.

3. A system according to claim 2 wherein the third volume is at least twenty times as large as the second volume.

4. A system according to claim 1 and further comprising a plasma generator associated with one or both of the first and second chambers.

5. A system according to claim 4 wherein the plasma generator is associated with the first chamber.

6. A system according to claim 1 wherein the first volume is at least ten times as large as the second volume.

7. A system according to claim 1 and further comprising a vent valve associated with the second chamber, and a control system associated with the vent valve wherein he vent valve can vent the system to a pressure lower than atmospheric pressure under the control of the control system.

8. A system according to claim 1 and further comprising a monitor associated with the second chamber capable of monitoring sterilant levels within the second chamber.

9. A system according to claim 1 and further comprising a temperature sensor and a pressure sensor associated with the second chamber.

10. A system according to claim 9 and further comprising a humidity sensor associated with the second chamber.

11. A system according to claim 1 and further comprising one or more additional chambers connected to the first chamber, each being separated therefrom by its own openable barrier.

12. A system according to claim 11 and further comprising a vent valve associated with each additional chamber and control system capable of independently controlling each of the vent valves associated with the additional chamber.

13. A method for providing a controlled sterilization or disinfection process suitable for collecting testing data, the method comprising the steps of:
providing a sterilizing environment comprising a vapor sterilant into a first chamber having a first volume;
placing a test device in a second chamber having a second volume;
opening a partition between the first chamber and the second chamber and thereby subjecting the second chamber to the sterilizing environment;
isolating the second chamber from the first chamber; and
after a predetermined time, quickly terminating exposure of the chemical sterilant to the test device, wherein the step of terminating the exposure of the chemical sterilant to the test device comprises withdrawing the chemical sterilant from the second chamber by exposing the second chamber to a source of vacuum which comprises a third volume at least five times as large as the second volume.

14. A method according to claim 13 wherein the third volume is at least ten times as large as the second volume.

15. A method according to claim 14 wherein the third volume is at least twenty times as large as the second volume.

16. A method according to claim 13 wherein the step of quickly terminating the exposure of the chemical sterilant to the test device comprises applying a plasma to the second chamber.

17. A method according to claim 16 wherein the plasma is generated in the first chamber and then admitted into the second chamber.

18. A method according to claim 13 and further comprising at some time prior to the predetermined time venting the second chamber to a pressure lower than atmospheric pressure.

19. A method according to claim 13 and further comprising the step of monitoring sterilant levels within the second compartment.

20. A method according to claim 13 wherein the test device comprises a biological indicator.

21. A method according to claim 13 wherein the test device comprises a chemical indicator.

22. A method according to claim 13 wherein the test device comprises a process challenge device.

* * * * *